US005602039A

United States Patent [19]

Van den Engh

[11] Patent Number: 5,602,039
[45] Date of Patent: Feb. 11, 1997

[54] FLOW CYTOMETER JET MONITOR SYSTEM

[75] Inventor: Ger Van den Engh, Seattle, Wash.

[73] Assignee: The University of Washington

[21] Appl. No.: 323,352

[22] Filed: Oct. 14, 1994

[51] Int. Cl.[6] .................................................. G01N 15/14
[52] U.S. Cl. ..................... 436/164; 436/63; 422/82.05; 435/2; 356/73; 250/461.2; 209/3.1; 209/3.3; 209/578; 209/579; 209/127.4
[58] Field of Search .................... 356/72, 73; 250/461.2; 209/3.1, 3.3, 571, 576–579, 552, 127.4, 906; 435/2, 7.24, 29; 436/52, 63, 164; 422/82.05, 82.08

[56] References Cited

U.S. PATENT DOCUMENTS

| | | | |
|---|---|---|---|
| 3,299,354 | 1/1967 | Hogg | 324/71 |
| 3,661,460 | 5/1972 | Elking et al. | 356/36 |
| 3,761,941 | 9/1973 | Robertson | 346/1 |
| 3,810,010 | 5/1974 | Thom | 324/71 |
| 3,826,364 | 7/1974 | Bonner | 209/3 |
| 3,960,449 | 6/1974 | Carleton et al. | 356/103 |
| 3,963,606 | 6/1976 | Hogg | 209/3 |
| 3,973,196 | 8/1976 | Hogg | 324/71 |
| 4,014,611 | 3/1977 | Simpson et al. | 356/72 |
| 4,070,617 | 1/1978 | Kachel et al. | 324/71 |
| 4,162,282 | 7/1979 | Fulwyler et al. | 264/9 |
| 4,230,558 | 11/1980 | Fulwyler | 209/3.1 |
| 4,302,166 | 11/1981 | Fulwyler et al. | 425/6 |
| 4,317,520 | 3/1982 | Lombardo et al. | 209/3.1 |
| 4,318,480 | 3/1982 | Lombardo et al. | 209/3.1 |
| 4,318,481 | 3/1982 | Lombardo et al. | 209/3.1 |
| 4,318,482 | 3/1982 | Barry et al. | 209/3.1 |
| 4,318,483 | 3/1982 | Lombardo et al. | 209/3.1 |

(List continued on next page.)

FOREIGN PATENT DOCUMENTS

| | | |
|---|---|---|
| 025296 | 3/1981 | European Pat. Off. . |
| 61-139747 | 6/1986 | Japan . |
| 61-159135 | 7/1986 | Japan . |
| 2024535 | 1/1990 | Japan . |
| 4126081 | 4/1992 | Japan . |
| 4126066 | 4/1992 | Japan . |
| 1056008 | 11/1983 | U.S.S.R. . |

OTHER PUBLICATIONS

Flow Cytometry and Cell Sorting, A. Radbruch (Ed.), "Operation of a Flow Cytometer" by Göttlinger et al., 1992, pp. 7–23.
Flow Cytometry: Instrumentation and Data Analysis, Van Dilla et al. (Eds.), "Overview of Flow Cytometry: Instrumentation and Data Analysis" by Martin Van Dilla, 1985, pp. 1–8.
Flow Cytometry: Instrumentation and Data Analysis, Van Dilla et al. (Eds.), "Flow Chambers and Sample Handling," by Pinkel et al., 1985, pp. 77–126.
Flow Cytometry and Sorting (1st Edition), Melamed, Mullaney, Mendelson, et al., John Wiley and Sons, 1979, pp. 3–9.

Primary Examiner—James C. Housel
Assistant Examiner—Rachel Heather Freed
Attorney, Agent, or Firm—Luke Santangelo

[57] ABSTRACT

A direct jet monitor illuminates the jet of a flow cytometer in a monitor wavelength band which is substantially separate from the substance wavelength band. When a laser is used to cause fluorescence of the substance, it may be appropriate to use an infrared source to illuminate the jet and thus optically monitor the conditions within the jet through a CCD camera or the like. This optical monitoring may be provided to some type of controller or feedback system which automatically changes either the horizontal location of the jet, the point at which droplet separation occurs, or some other condition within the jet in order to maintain optimum conditions. The direct jet monitor may be operated simultaneously with the substance property sensing and analysis system so that continuous monitoring may be achieved without interfering with the substance data gathering and may be configured so as to allow the front of the analysis or free fall area to be unobstructed during processing.

40 Claims, 3 Drawing Sheets

5,602,039
Page 2

U.S. PATENT DOCUMENTS

| | | | |
|---|---|---|---|
| 4,325,483 | 4/1982 | Lombardo et al. | 209/3.1 |
| 4,361,400 | 11/1982 | Gray et al. | 356/23 |
| 4,395,676 | 7/1983 | Hollinger et al. | 324/71.4 |
| 4,487,320 | 11/1984 | Auer | 209/3.1 |
| 4,515,274 | 5/1985 | Hollinger | 209/3.1 |
| 4,538,733 | 9/1985 | Hoffman | 209/3.1 |
| 4,631,483 | 12/1986 | Proni et al. | 324/71.4 |
| 4,673,288 | 6/1987 | Thomas et al. | 356/72 |
| 4,691,829 | 9/1987 | Auer | 209/3.1 |
| 4,818,103 | 4/1989 | Thomas et al. | 356/72 |
| 4,845,025 | 7/1989 | Lary et al. | 435/2 |
| 4,981,580 | 1/1991 | Auer | 209/3.1 |
| 4,983,038 | 1/1991 | Ohki et al. | 356/246 |
| 5,005,981 | 4/1991 | Schulte et al. | 366/219 |
| 5,007,732 | 4/1991 | Ohki et al. | 356/73 |
| 5,079,959 | 1/1992 | Miyake et al. | 73/864.85 |
| 5,144,224 | 9/1992 | Larsen | 327/71.4 |
| 5,159,397 | 10/1992 | Kosaka et al. | 250/461.2 |
| 5,159,403 | 11/1992 | Kosaka | 356/243 |
| 5,167,926 | 11/1992 | Kimura et al. | 422/67 |
| 5,182,617 | 1/1993 | Yoneyama et al. | 356/440 |
| 5,199,576 | 4/1993 | Corio | 209/564 |
| 5,215,376 | 6/1993 | Schulte et al. | 366/348 |
| 5,247,339 | 9/1993 | Ogna | 356/73 |
| 5,259,593 | 11/1993 | Orme et al. | 266/78 |
| 5,260,764 | 11/1993 | Fukuda et al. | 356/73 |
| 5,359,907 | 11/1994 | Baker et al. | 73/865.5 |
| 5,370,842 | 12/1994 | Miyazaki et al. | 422/82.06 |
| 5,412,466 | 4/1995 | Ogino | 356/246 |

FLOW CYTOMETER JET MONITOR SYSTEM

BACKGROUND OF THE INVENTION

This invention relates to flow cytometers as are used in clinical and research applications. Specifically, the invention relates to systems which monitor the conditions of the jet emitted from a nozzle in a flow cytometer during the processing operation. The invention may be applied regardless of the type of processing involved and is particularly appropriate for sorting and analysis applications.

Flow cytometers have been in clinical and research use for many years. Basically, the systems act to position small amounts of a substance within a sheath fluid. This sheath fluid may either form droplets or may exist in a jet for optical analysis. Through hydrodynamic focusing and laminar flow, the substance is split into individual cells and the like and is surrounded by a sheath fluid. In many applications, the sheath fluid together with its entrained substance exits a nozzle in a jet and either free falls or is channeled in an optically transparent pathway for analysis. This analysis requires very precise and uniform conditions within the jet. Unfortunately, variations do still exist. Thus, there has been a need to monitor the conditions of the jet in order to assure accurate analysis. Two types of variations are of particular concern. First, the breakoff point at which droplet formation occurs tends to vary or drift. This exists as a result of changes in material, temperatures, the existence of air bubbles, and the like as those skilled in the art well know. Since the exact location of the droplet separation point is utilized for differentially charging various droplets and other aspects, such variations can destroy the ability to achieve the desired function of the flow cytometer.

The change in droplet separation point has been the subject of a number of inventions. As U.S. Pat. Nos. 4317520, 4318480, 4,318,481, 4,318,482, 4,318,483, and 4,325,483 explain, traditionally the approach has been to determine the droplet separation point through the use of a strobe light and microscopic analysis prior to the actual processing of the substance. The processing is then conducted based upon the location determined for the droplet separation point under the assumption that no drift or variation occurs. Obviously, this type of approach does not recognize the realities of actual processing and totally ignores the fact that variation in the location of the droplet separation point does, in fact, occur.

As U.S. Pat. Nos. 4,317,520, 4,318,480, 4,318,481, 4,318, 482, 4,318,483, and 4,325,483 further explain, one approach taken has been to utilize the amount of scatter of the light emitted from a laser fluorescent source as an indirect indication of the location at which the surface tension "pinching" (and thus the droplet formation) is occurring. This approach has the significant advantage of affording the opportunity to actually monitor the conditions during processing, however, it does not provide a direct indication of the condition. While a great improvement over the traditional approach, the approach these related patents take still appears to provide only an indirect—and somewhat less accurate—indication of the exact location of the droplet separation point. Further, these references also suggest illumination of the sheath fluid at a wavelength where the sheath fluid is translucent. This can be unnecessary.

Similarly, related U.S. Pat. Nos. 4,691,829 and 4,487,320 suggest the use of scattered light as an indirect indication of the droplet separation point. These two references each explain that while a direct indication of the droplet separation point would be desirable, a physical limitation makes this impractical. Basically, they explain that the presence of undesired light destroys the ability to gather the data desired, namely, the emissions from the substance itself.

A second type of variation in the conditions within the jet which is of concern is the fact that the jet can tend to move horizontally. This is true even for systems in which the jet is channeled. While, naturally, the nozzle container is usually fixed, the same type of variations which cause change in the droplet separation point can also cause the jet to be directed to one side or the other. While this amount of variation can be relatively small, it still poses an unnecessary degradation in the signal sensed as it can change the focal point and otherwise destroy resolution accuracies. None of the references mentioned seem to have addressed this aspect.

One of the practical problems which has also been recognized is the fact that only a limited amount of space exits within which to conduct monitoring and sensing. As Japanese Patent 2024535 recognizes with respect to the sensing system alone, it is desirable to have an optical system which is as small as possible. The present invention achieves this as well as other goals.

As mentioned, there has been a long felt but unsatisfied need for a device which permits accurate and direct monitoring of the conditions within the jet of a flow cytometer during the processing operation. As the present invention shows, such a system is, indeed, possible and, in fact, can be implemented using arts and elements which had long been available. To some extent, apparently solutions had not been achieved because those skilled in the art seem to have taken a direction which was away from the technical direction pursued in the present invention. This may have been the result of the fact that those skilled in the art did not truly appreciate the nature of the problem or may have been the result of the fact that those skilled in the art were misled by some of the presumptions and assumptions with respect to the type of systems which could be considered. In this regard, it had been assumed that direct monitoring through the use of some illumination source or some optical source was not practical because of an inevitable interference with the sensing system. The present invention shows that this is not the case and that direct monitoring can be achieved without the interference. Not only in this regard but in other facets as well, the present invention demonstrates that although substantial attempts had been made by those skilled in the art in order to achieve a practical monitoring system, the direction of the present invention was not recognized. Until the present invention, a system which allowed direct monitoring of jet conditions was not practically achievable.

SUMMARY OF THE INVENTION

The invention discloses a direct monitoring system which provides a separate illumination source for the direct sensing of the conditions of the jet in a flow cytometer. The illumination source may be selected to exist at a wavelength (such as the infrared wavelength) which does not overlap with either a substance stimulation source or a substance property sensor. In addition, a compact charge coupled device (CCD) camera can be utilized in conjunction with an infrared source to directly monitor the conditions of the jet while simultaneously stimulating the substance through a laser source and sensing fluorescence. Although these conditions exist simultaneously, the present invention shows that no interference exists and also shows that the system can be designed so as to be sufficiently compact as to leave the entire front of the jet unobstructed.

Accordingly, it is an object of the invention to allow for direct monitoring during the processing operation of flow cytometry. In keeping with this object, a goal is to provide an optical image of the actual droplet separation point and jet stream to allow very accurate determination of its location.

Another broadly stated object of the invention is to permit monitoring without impacting the quality of the measurements made by the flow cytometer system. This object has as a goal providing a monitoring system which utilizes wavelengths and bands which are substantially separate from the frequencies and bandwidths used for both substance stimulation and substance sensing.

Yet another object of the invention is to provide for a design which minimizes the space requirements in the vicinity of the jet. In keeping with this object, a goal is to configure each of the light sources and their respective sensors away from the front of the flow cytometer jet.

Yet another object is to provide for a system which is easily manufacturable and economically implemented. Thus, a goal is to utilize compact devices such as a CCD camera in the vicinity of the flow cytometer jet stream.

Naturally, further objects of the invention are disclosed throughout other areas of the specification and claims.

DETAILED DESCRIPTION OF THE PREFERRED EMBODIMENT

Figure 1:
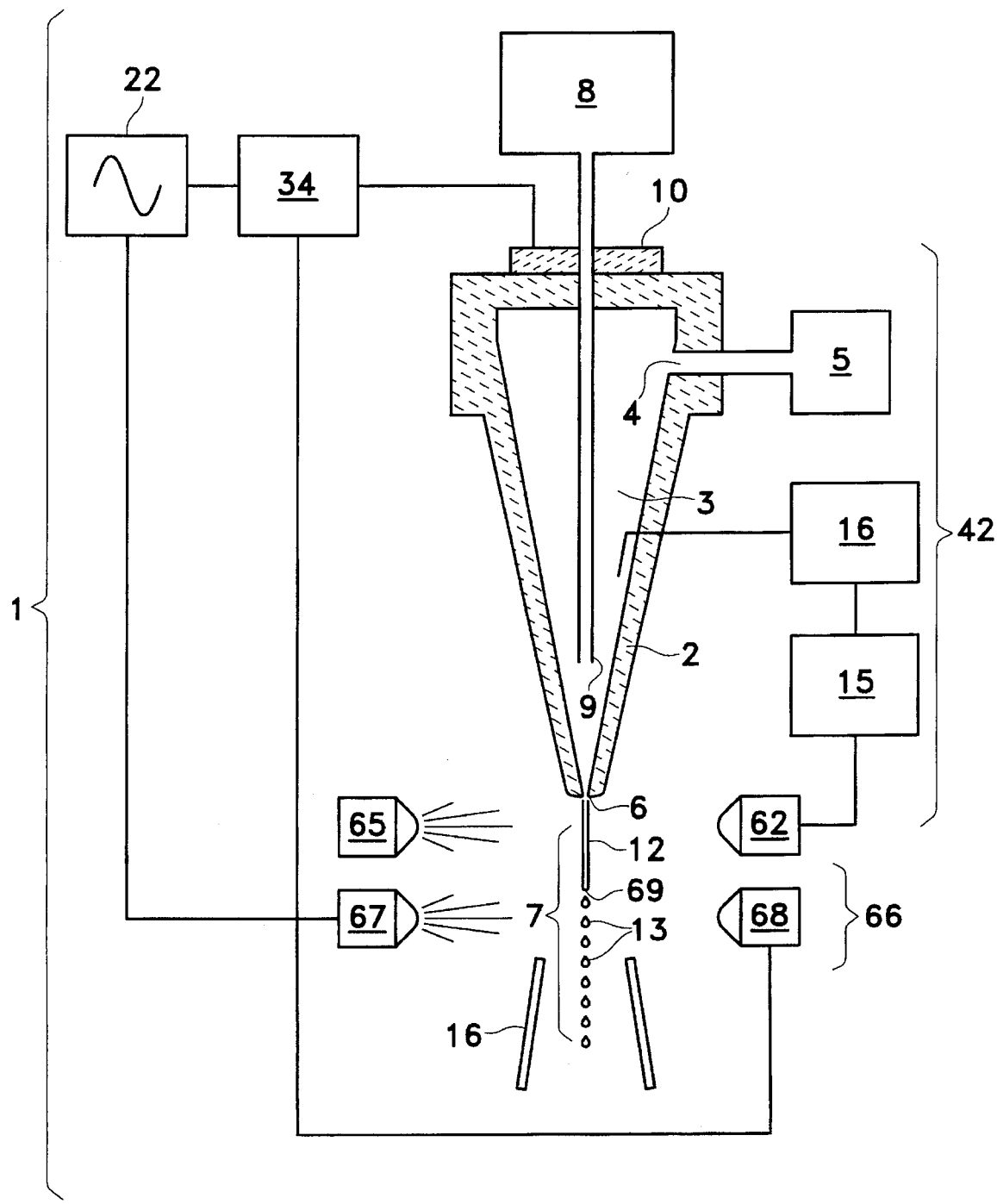
FIG. 1 is a schematic cross-sectional view of a direct jet monitor as applied to a droplet flow cytometer.
Figure 2:
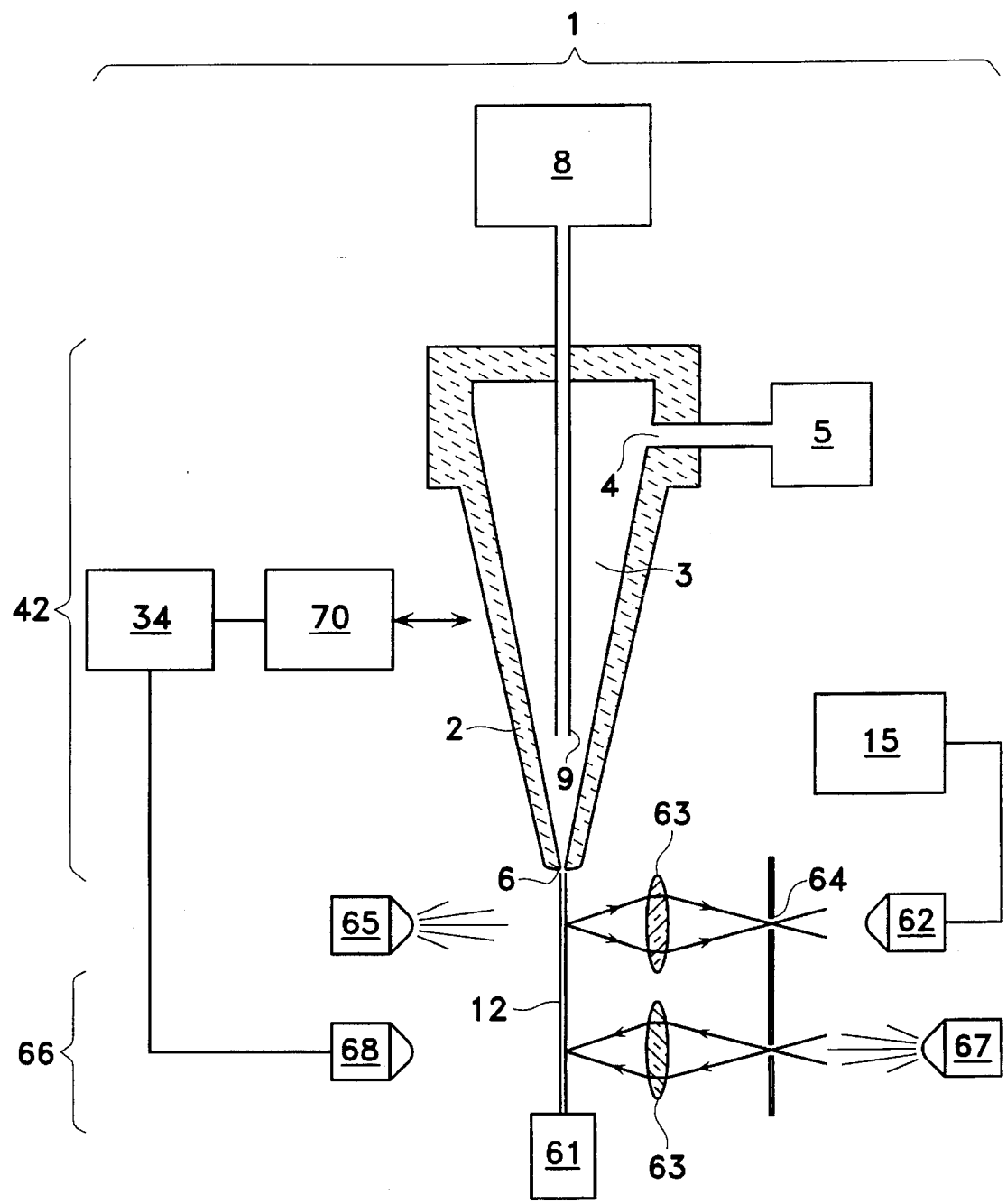
FIG. 2 is a schematic cross-sectional view of a direct jet monitor as applied to a continuous jet flow cytometer.

Referring to FIGS. 1 and 2, it can be seen how the present invention provides a monitoring system which may be implemented in conjunction with either a droplet flow cytometer or a continuous jet flow cytometer. In either configuration, the flow cytometer (1) involves a nozzle system (42) which acts to introduce a flow of a substance within a sheath fluid. To accomplish this, nozzle system (42) includes nozzle container (2) which establishes nozzle volume (3). Nozzle volume (3) has sheath fluid port (4) within it so that a sheath fluid may be introduced to it from sheath reservoir (5). In addition, a substance introduction port (9) is included so that a substance may be introduced from substance reservoir (8) within the sheath fluid. The sheath fluid, together with its entrained substance are then hydrodynamically focused so that single cells and the like may be emitted from nozzle exit (6) into free fall area (7) or an analysis below. [By the term "below" it should be understood that the area need only occur after nozzle exit (6) and need not be strictly gravitationally under nozzle exit (6) since channel system can be oriented horizontally.] By allowing the sheath fluid to exit from nozzle volume (3), jet (12) is created. This jet occurs within free fall area (7) or an analysis area where it may be analyzed or further processed.

In a droplet flow cytometer as shown in FIG. 1, a vibration in jet (12) may be initiated by oscillator (10). Oscillator (10) acts to initiate variations within jet (12) so that its oscillations may act to form droplets (13) from the sheath fluid as those skilled in the art readily understand. Each of the droplets (13) may be differentially analyzed in an analysis area to assess whether they contain a particular item of substance such as a cell or a cell fragment. For a sorting application, sorting equipment (16) may be included to differentially charge each droplet which contains a substance and thus deflect them electrostatically. In the continuous jet flow cytometer shown in FIG. 2, the jet may simply be analyzed in an analysis area and collected in some receptacle (61). In this area the jet may either be contained with a channel or it may free fall.

Importantly, most flow cytometers act to sense a specific property of the substance being analyzed. In the type of flow cytometers involved in this invention, this can occur within free fall area (7) or an analysis area. As shown in FIGS. 1 and 2, this occurs through the use of some type of substance property sensor (62). Substance property sensor (62) may be positioned so that it senses emissions occurring from the substance within jet (12). The signals then sensed may be utilized by analysis equipment (15) in host of different ways depending upon the particular substance or application involved. Substance property sensor (62) may sense direct signals from jet (12) as shown in FIG. 1 or may include one or more lens (63) which may direct the light through aperture (64) as shown in FIG. 2. Additionally, it may be understood that the emissions from the substance may occur at one wavelength or frequency or may occur throughout a substance wavelength band. Naturally, substance property sensor (62) should be responsive to the particular emissions desired and thus should operate in the substance wavelength band when appropriate.

In order to analyze the substance, it is frequently common to cause fluorescence of the substance and then analyze its emissions. This may be created naturally or by stimulating the substance after it exits from nozzle container (2) through some type of substance stimulation source (65). Substance stimulation source (65) should be directed towards the substance possibly at location of jet (12). As those skilled in the art would readily understand, substance stimulation source (65) may emit electromagnetic radiation and thus serve as an electromagnetic source such as a laser which causes the substance to fluoresce. This fluorescence may occur within a fluorescence emission band.

Since both the fluorescence emission band and the wavelengths at which substance stimulation source (65) operates in order to cause fluorescence are typically in the visible spectrum, those skilled in the art have been apparently led to the conclusion that optical monitoring was not practical without interference. The present invention shows this not to be the case. Specifically, it can be seen in both FIGS. 1 and 2 that the design includes direct jet monitor (66) positioned adjacent to substance property sensor (62). As shown in both figures, direct jet monitor (66) may include jet illumination source (67) which may direct electromagnetic emissions within a monitor wavelength band towards an analysis area (such as free fall area (7)) and jet (12). As shown in FIG. 1, it can be seen that the electromagnetic emissions of jet illumination source (67) may to some extent illuminate substance property sensor (62). While those skilled in the art had previously considered that such illumination would cause undesirable interference, the present invention shows how this may be avoided entirely. Instead of avoiding an optical image, direct jet monitor (66) acts to optically sense and monitor conditions within jet (12). These conditions may include the jet's location or its drop separation point (69) among other parameters. This monitoring can occur simultaneously with the sensing of a substance property as the substance passes through jet (12). The technique of directly monitoring these conditions without interfering with the substance sensing affords greater precision in ascertaining the actual conditions of jet (12). Unlike the approaches previously taken, direct jet monitor (66) does not sense only an indirect indication such as the light scattered. Instead direct jet monitor (66) is capable of directly imaging the shape and condition of jet (12). Rather than merely providing an indirect indication which suggests that a condition within jet (12) has changed, direct jet monitor (66) is configured so as to provide an affirmative image of jet (12). This image may be processed or displayed depending upon the application. Through the use of jet illumination source (67), jet (12) is thus illuminated in order to permit a direct conclusion with respect to at least one condition within jet (12).

In order to permit optical sensing of jet (12), ambient light might be able to be used for some applications, however, it is replaced by a separate source in the preferred embodiment. Thus, illumination of jet (12) is accomplished while simultaneously allowing data measuring to occur. To avoid interference, jet illumination source (67) may be configured as an infrared source. This infrared source may act to subject the jet to infrared radiation which exists within a monitor wavelength band which is substantially separate from the wavelength bands and frequencies utilized by substance property sensor (62) or substance stimulation source (65). Since many substances fluoresce in the 400 nm to 800 nm range, and since many lasers or other sources stimulate such fluorescence by emitting in the 200 nm to 800 nm range, making the monitor wavelength band exist in the infrared range (800 nm to 3000 nm) avoids any overlap with these bands. By keeping the monitor wavelength band and the fluorescence emission band substantially separate—that is, having little or no overlap and thus little or no interference—both direct jet monitor (66) and substance property sensor (62) may simultaneously operate and yet be independent of each other.

As mentioned, jet illumination source (67) may actually be an infrared source. Correspondingly, direct jet monitor (66) may include some type of jet condition sensor (68) which responds to the particular frequency emitted by jet illumination source (67). In order to save space and enhance the manufacturing economies, jet condition sensor (68) may actually be some type of charge coupled device such as a CCD camera. Thus, the CCD camera is activated by the infrared source and is responsive to it. It receives emissions in and is responsive to the monitor wavelength band. Since the monitor wavelength band is substantially separate from the fluorescence emission band or the substance wavelength band and is separate from the substance stimulation band (the wavelength or band at which the substance may be stimulated to fluoresce), both direct jet monitor (66) and substance property sensor (62) may be simultaneously operated.

The operation of direct jet monitor (66) simultaneously with substance property sensor (62) affords the opportunity to feedback to the system the conditions and to make corrections in the system. This may be accomplished in the design shown in FIGS. 1 and 2 through the use of some controller (34). As shown, it can be seen that controller (34) is responsive to direct jet monitor (66). This may be through attachment or electrical connection to jet condition sensor (68). When jet condition sensor (68) makes some type of determination with respect to the condition within jet (12), its output may be used to adjust at least one condition within the jet as those skilled in the art could readily implement. This adjustment may actually be an adjustment of some parameter giving rise to the jet such as the location of nozzle container (2) as shown in FIG. 2 or the control of oscillator (10) (such as a piezoelectric crystal) as shown in FIG. 1. In each situation, controller (34) may respond to suboptimum conditions and act to correct them.

As shown in FIG. 1, controller (34) is connected to oscillator (10) and in this fashion can control the location at which the droplet separation point (69) occurs. As those skilled in the art well know, this is because oscillator (10) acts to cause droplets (13). The oscillator (10) shown is controlled by alternating voltage source (22) which acts as an oscillator drive. When this oscillator drive applies an alternating voltage to oscillator (10), oscillations occur within the sheath fluid in a manner which causes droplet (13). By making oscillator (10) responsive to jet condition sensor (68), controller (34) may act to vary the amplitude supplied from alternating voltage source (22) to oscillator (10). Again, the circuiting to implement this could be easily designed. In this fashion, the amplitude of the pressure wave within the sheath fluid may be varied in a manner which adjusts the location at which the droplet separation point (69) occurs. Since the sheath fluid is responsive to oscillator (10), controller (34) acts to adjust the location at which droplet separation point (69) occurs and thus can automatically achieve adjustment in a feedback arrangement.

As also shown in FIG. 1, it should be understood that alternating voltage source (22) may have a characteristic frequency which is unvaried. This frequency may be determined by the arrangement of the nozzle system. Since it may be desirable to strobe jet illumination source (67), it can be seen that jet illumination source (67) is connected directly to alternating voltage source (22). Thus, the frequency at which oscillator (10) operates and the frequency at which jet illumination source (67) operate are identical. Since droplets (13) are formed based upon the frequency of oscillator (10), this can effect a simple stroboscopic arrangement whereby the conditions within jet (12) can be precisely monitored.

As shown in FIG. 2, it can be seen how an alternative feedback arrangement may be configured for a continuous jet flow cytometer. In that figure, jet condition sensor (68) is connected to controller (34). This in turn may be connected to one or more nozzle adjuster (70) which acts to move nozzle container (2) horizontally. Further, when arranged orthogonally and the like, this horizonal movement can be throughout the horizontal plane. By adjusting the location of nozzle volume (3), nozzle adjuster (70) can correct for the horizontal location of jet (12) as required.

In order to accurately sense a change in the horizontal location, it may be understood how the arrangement of FIG. 2 is configured. Through the use of a lens (63) arranged within the light being emitted by jet illumination source (67), a focal point which corresponds horizontally to that arranged for substance property sensor (62) may be created. This focal point is within jet (12). Thus, when the jet (12) becomes out of focus, jet monitor sensor (68) may sense this and provide a signal to controller (34) which may in turn cause movement of nozzle volume (3) through the operation of nozzle adjuster (70). Since the amount of movement may be small—on the order of one micron or so—the conditions of jet (12) may be adjusted so as to optimize the analysis capabilities of flow cytometer (1).

Figure 3:
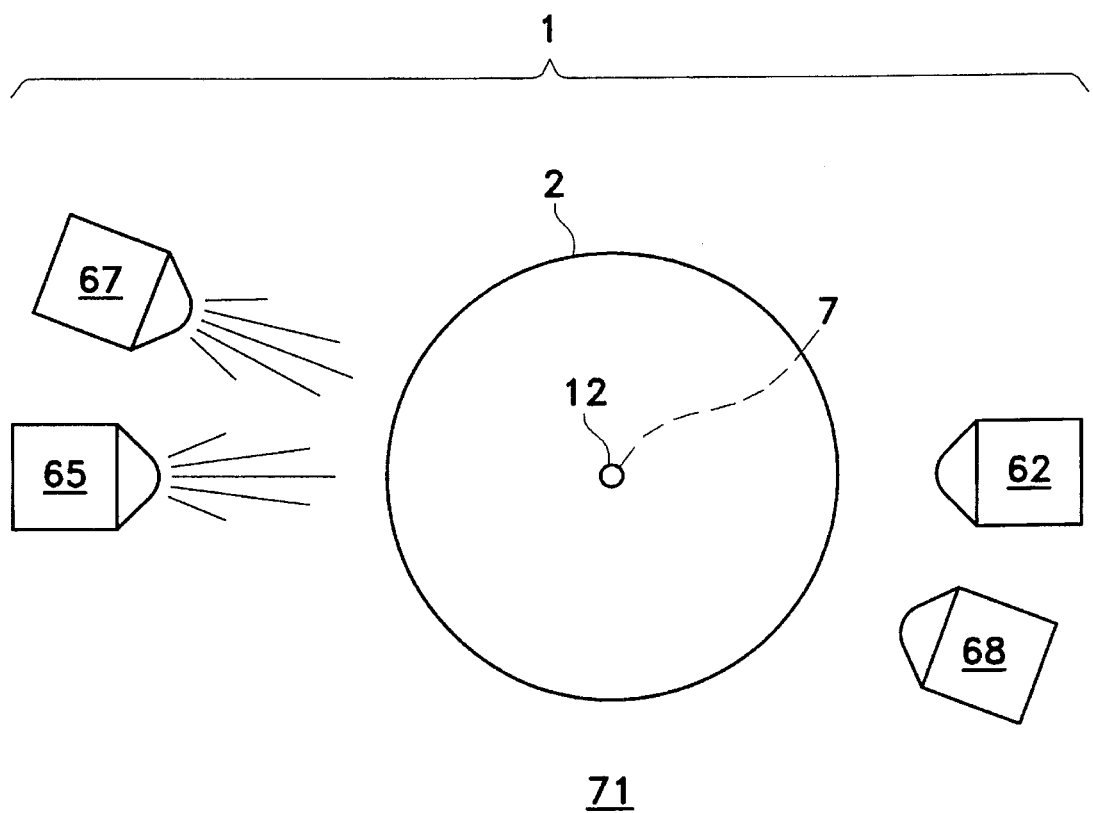
FIG. 3 is a top view of an embodiment of showing the configuration to avoid the front of the free fall or analysis area.

Finally, referring to FIG. 3, it can be understood how both substance property sensor (62) and its corresponding substance stimulation source (65) may be arranged together with jet illumination source (67) and its corresponding jet condition sensor (68) to avoid front (71) of analysis or free fall area (7) (the area which faces the operator). By configuring these devices and utilizing small devices such as the CCD camera or the infrared source, this arrangement may afford the opportunity to observe the flows within flow cytometer (1) without undue obstruction.

The foregoing discussion and the claims which follow describe the preferred embodiment of the invention. Particularly with respect to the claims it should be understood that changes may be made without departing from their essence. In this regard, it is intended that such changes would still fall within the scope of this patent. It simply is not practical to describe and claim all possible revisions which may be accomplished for the varying applications. To the extent the revisions utilize the essence of the present invention each would naturally fall within the breath of protection encompassed by this patent.

I claim:

1. A flow cytometer system which monitors jet conditions comprising:
   a. a nozzle container establishing a nozzle volume and having a nozzle exit;
   b. a sheath fluid port located within said nozzle volume;
   c. a substance introduction port located within said nozzle volume;
   d. an analysis area below said nozzle exit wherein a jet occurs;
   e. a substance property sensor which senses emissions from said analysis area over a substance wavelength band;
   f. a jet illumination source directed towards said analysis area and which emits electromagnetic emissions over a monitor wavelength band which is substantially separate from said substance wavelength band; and
   g. a jet condition sensor which receives emissions from said analysis area and which is responsive to said monitor wavelength band.

2. A flow cytometer system which monitors jet conditions as described in claim 1 and further comprising a substance stimulation source directed towards said analysis area.

3. A flow cytometer system which monitors jet conditions as described in claim 2 wherein said substance introduction port introduces a substance and wherein said substance stimulation source comprises an electromagnetic source which causes fluorescence in said substance.

4. A flow cytometer system which monitors jet conditions as described in claim 3 wherein said fluorescence occurs in a fluorescence emission band and wherein said monitor wavelength band is substantially separate from said fluorescence emission band.

5. A flow cytometer system which monitors jet conditions as described in claim 4 wherein said jet illumination source comprises an infrared source.

6. A flow cytometer system which monitors jet conditions as described in claim 5 wherein said jet condition sensor comprises a charge coupled device which is responsive to said infrared source.

7. A flow cytometer system which monitors jet conditions as described in claim 6 wherein said electromagnetic source comprises a laser source.

8. A flow cytometer system which monitors jet conditions as described in claim 7 wherein said analysis area has a front, wherein said infrared source, said charge coupled device, said substance property sensor, and said laser source are configured away from said analysis front.

9. A flow cytometer system which monitors jet conditions as described in claim 1, 3, 5, or 7 and further comprising a controller which is responsive to said jet condition sensor and wherein said controller acts to adjust at least one condition within said jet.

10. A flow cytometer system which monitors jet conditions as described in claim 9 and further comprising a nozzle adjuster connected to said nozzle container and connected to said controller which adjusts the location of said nozzle container.

11. A flow cytometer system which monitors jet conditions as described in claim 1, 3, 5 or 7 and further comprising an oscillator to which said sheath fluid is responsive and which acts to cause droplets in said jet at a droplet separation point.

12. A flow cytometer system which monitors jet conditions as described in claim 11 and further comprising a controller which is responsive to said jet condition sensor and wherein said controller acts to adjust the location at which said droplet separation point occurs.

13. A flow cytometer system which monitors jet conditions as described in claim 12 and further comprising an oscillator drive connected to said oscillator and connected to said controller.

14. A flow cytometer system which monitors jet conditions as described in claim 13 wherein said oscillator drive comprises an alternating voltage source having an amplitude and wherein said controller adjusts said amplitude.

15. A flow cytometer system which monitors jet conditions comprising:
   a. a nozzle container establishing a nozzle volume and having a nozzle exit;
   b. a sheath fluid port located within said nozzle volume;
   c. a substance introduction port located within said nozzle volume;
   d. an analysis area below said nozzle exit wherein a jet occurs;
   e. a substance property sensor which senses emissions from said analysis area over a substance wavelength band; and
   f. a direct jet monitor responsive to said jet and which operates simultaneously with said substance property sensor wherein said jet monitor emits a substantially separate wavelength band from said substance wavelength band.

16. A flow cytometer system which monitors jet conditions as described in claim 15 wherein said direct jet monitor comprises an optical sensor.

17. A flow cytometer system which monitors jet conditions as described in claim 16 wherein said direct jet monitor further comprises an infrared source.

18. A flow cytometer system which monitors jet conditions as described in claim 17 wherein said optical sensor comprises a charge coupled device.

19. A flow cytometer system which monitors jet conditions as described in claim 18 and further comprising:
   a. an oscillator to which said sheath fluid is responsive and which acts to cause droplets in said jet at a droplet separation point;
   b. an alternating voltage source having an amplitude; and
   c. a controller which adjusts said amplitude in response to said direct jet monitor.

20. A flow cytometer system which monitors jet conditions as described in claim 18 and further comprising a nozzle adjuster connected to said nozzle container and responsive to said direct jet monitor which adjusts the location of said nozzle container.

21. A method of droplet flow cytometry which monitors the condition of the jet comprising the steps of:
   a. establishing a nozzle volume;
   b. introducing a flow of sheath fluid into said nozzle volume;
   c. introducing a flow of a substance within said sheath fluid in said nozzle volume;
   d. allowing said sheath fluid to exit from said nozzle volume into an analysis area to create a jet;
   e. sensing a property of said substance in a substance wavelength band;
   f. illuminating said jet in said analysis area in a monitor wavelength band which is substantially separate from said substance wavelength band; and
   g. monitoring at least one jet condition in said analysis area in said monitor wavelength band.

22. A method of droplet flow cytometry which monitors the condition of the jet as described in claim 21 and further comprising the step of stimulating said substance after it exits from said nozzle volume.

23. A method of droplet flow cytometry which monitors the condition of the jet as described in claim 22 wherein said step of stimulating said substance after it exits from said nozzle volume comprises the step of causing said substance to fluoresce in a fluorescence emission band and wherein said step of sensing a property of said substance comprises the step of sensing emissions in said fluorescence emission band.

24. A method of droplet flow cytometry which monitors the condition of the jet as described in claim 23 wherein said monitor wavelength band is substantially separate from said fluorescence emission band.

25. A method of droplet flow cytometry which monitors the condition of the jet as described in claim 24 wherein said step of illuminating said jet in said analysis area comprises the step of subjecting said jet to infrared radiation.

26. A method of droplet flow cytometry which monitors the condition of the jet as described in claim 25 wherein said step of monitoring at least one jet condition in said analysis area comprises the step of activating a charge coupled device.

27. A method of droplet flow cytometry which monitors the condition of the jet as described in claim 26 wherein said step of stimulating said substance after it exits from said nozzle volume comprises the step of directing a laser at said substance.

28. A method of droplet flow cytometry which monitors the condition of the jet as described in claim 21, 23, 25, or 27 and further comprising the step of Controlling at least one condition within said nozzle volume in response to said step of monitoring at least one jet condition in said analysis area.

29. A method of droplet flow cytometry which monitors the condition of the jet as described in claim 28 wherein said step of controlling at least one condition within said nozzle volume in response to said step of monitoring at least one jet condition in said analysis area comprises the step of adjusting the location of said nozzle volume.

30. A method of droplet flow cytometry which monitors the condition of the jet as described in claim 21, 23, 25, or 27 and further comprising the step of establishing an oscillation which acts to cause droplets in said jet at a droplet separation point.

31. A method of droplet flow cytometry which monitors the condition of the jet as described in claim 30 and further comprising the step of controlling the location at which said droplet separation point occurs in response to said step of monitoring at least one jet condition in said analysis area.

32. A method of droplet flow cytometry which monitors the condition of the jet as described in claim 31 wherein said step of establishing an oscillation is responsive to said step of controlling the location at which said droplet separation point occurs.

33. A method of droplet flow cytometry which monitors the condition of the jet as described in claim 32 wherein said step of establishing an oscillation comprises the step of applying an alternating voltage having an amplitude to an oscillator and wherein said step of controlling the location at which said droplet separation point occurs comprises the step of varying said amplitude of said alternating voltage.

34. A method of droplet flow cytometry which monitors the condition of the jet comprising the steps of:
   a. establishing a nozzle volume;
   b. introducing a flow of sheath fluid into said nozzle volume;
   c. introducing a flow of a substance within said sheath fluid in said nozzle volume;
   d. allowing said sheath fluid to exit from said nozzle volume into an analysis area to create a jet;
   e. sensing a property of said substance in a substance wavelength band; and
   f. directly monitoring conditions in said jet while accomplishing said step of sensing a property of said substance in a substance wavelength band wherein said step of directly monitoring Conditions in said jet comprises the step of illuminating said jet in said analysis area in a monitor wavelength band which is substantially separate from said substance wavelength band.

35. A method of droplet flow cytometry which monitors the condition of the jet as described in claim 34 wherein said step of directly monitoring conditions in said jet comprises the step of optically sensing said conditions from said jet without interfering with said step of sensing a property of said substance in a substance wavelength band.

36. A method of droplet flow cytometry which monitors the condition of the jet as described in claim 35 wherein said step of directly monitoring conditions in said jet comprises the step of sensing said monitor wavelength band after it passes through a portion of said analysis area.

37. A method of droplet flow cytometry which monitors the condition of the jet as described in claim 36 wherein said step of illuminating said jet in said analysis area in a monitor wavelength band comprises the step of subjecting said jet to infrared radiation.

38. A method of droplet flow cytometry which monitors the condition of the jet as described in claim 36 wherein said step of sensing said monitor wavelength band after it passes through a portion of said analysis area comprises the step of activating a charge coupled device.

39. A method of droplet flow cytometry which monitors the condition of the jet as described in claim 38 and further comprising the steps of:
   a. applying an alternating voltage having an amplitude to an oscillator; and
   b. adjusting said amplitude of said alternating voltage in response to said step of directly monitoring conditions in said jet.

40. A method of droplet flow cytometry which monitors the condition of the jet as described in claim 38 and further comprising the step of adjusting the location of said nozzle in response to said step of directly monitoring conditions in said jet.

* * * * *

UNITED STATES PATENT AND TRADEMARK OFFICE
CERTIFICATE OF CORRECTION

PATENT NO. : 5,602,039
DATED : February 11, 1997
INVENTOR(S) : Van den Engh, Ger

It is certified that error appears in the above-indentified patent and that said Letters Patent is hereby corrected as shown below:

Column 1, line 4, insert the following information:

-- The U.S. Government has a paid-up license in this invention and the right in limited circumstances to require the patent owner to license others on reasonable terms as provided for by the terms of a contract number DE-FG06-93ER-61662 awarded by the Department of Energy.--

Signed and Sealed this

Eighth Day of July, 1997

*Attest:*

BRUCE LEHMAN

*Attesting Officer*     *Commissioner of Patents and Trademarks*